United States Patent
Feldman et al.

(10) Patent No.: US 6,539,278 B1
(45) Date of Patent: Mar. 25, 2003

(54) METHOD AND APPARATUS FOR RESIN FORMULATIONS WITH IMPROVED STREAKING PERFORMANCE

(75) Inventors: Sandra Freedman Feldman, Niskayuna, NY (US); Andrew Joseph Poslinski, Niskayuna, NY (US); Vicki Herzl Watkins, Alplaus, NY (US); James Paul Barren, Scotia, NY (US); Arthur Joseph Osborn, Catskill, NY (US); John Frederick Graf, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/398,280

(22) Filed: Sep. 20, 1999

(65) Prior Publication Data (65)

(51) Int. Cl.⁷ .............................................. G06F 19/00
(52) U.S. Cl. ................... 700/204; 700/197; 356/237.1
(58) Field of Search ........................... 700/204, 197; 356/237.1, 239.7, 430; 425/173, 172, 140, 141

(56) References Cited

U.S. PATENT DOCUMENTS

| | | | | |
|---|---|---|---|---|
| 3,988,403 A | * | 10/1976 | Angell et al. ............ 356/237.2 |
| 4,629,319 A | * | 12/1986 | Clarke et al. ............ 356/237.2 |
| 5,745,238 A | * | 4/1998 | Long et al. ................. 356/601 |
| 5,859,708 A | * | 1/1999 | Feldman ..................... 356/406 |
| 5,900,259 A | * | 5/1999 | Miyoshi et al. ............. 425/145 |
| 5,943,127 A | * | 8/1999 | Feldman et al. ......... 356/237.2 |
| 6,005,668 A | * | 12/1999 | Held et al. .................. 356/600 |
| 6,078,398 A | * | 6/2000 | Feldman et al. ............ 356/402 |
| 6,258,301 B1 | * | 7/2001 | Feuerherm et al. ........ 264/40.1 |
| 6,259,093 B1 | * | 7/2001 | Wakiyama et al. ......... 250/306 |
| 2002/0015148 A1 | * | 2/2002 | Tomomatsu ............. 356/237.2 |

* cited by examiner

Primary Examiner—Leo Picard
Assistant Examiner—Chad Rapp
(74) Attorney, Agent, or Firm—Patrick K. Patnode; Christian G. Cabou

(57) ABSTRACT

Using the molding tool (2), spatially-resolved spectrometer (1) and computerized device (101) of U.S. patent application Ser. No. 09/303,409, streaking problems identified in production are first diagnosed (140), then duplicated on a laboratory scale (142) and compared with the streaking problems observed in production. Next, options are developed and tested for fixing (correcting) the observed problem and testing these on a laboratory scale (144). Finally, the option(s) chosen for correcting the observed problem are validated prior to reinitiating full-scale production (146).

28 Claims, 15 Drawing Sheets

FIG. 7 Description of signal peaks
L vs x positon for compressed and first iteration of peak and valley detection data FIG. 8  Description of signal peaks
L vs x position for first and second iteration of peak and valley detection FIG. 9  Description of signal peaks
L vs x postion for second iteration and third iteration of peak and valley detection Description of signal peaks

FIG. 12 L Shift Calculation ( similar for a shift and b shift clcultions)

FIG. 13 L Shift Calculation (similar for a shift and b shift calculations)

Diagnose Initial Streaking Problem *(140)*
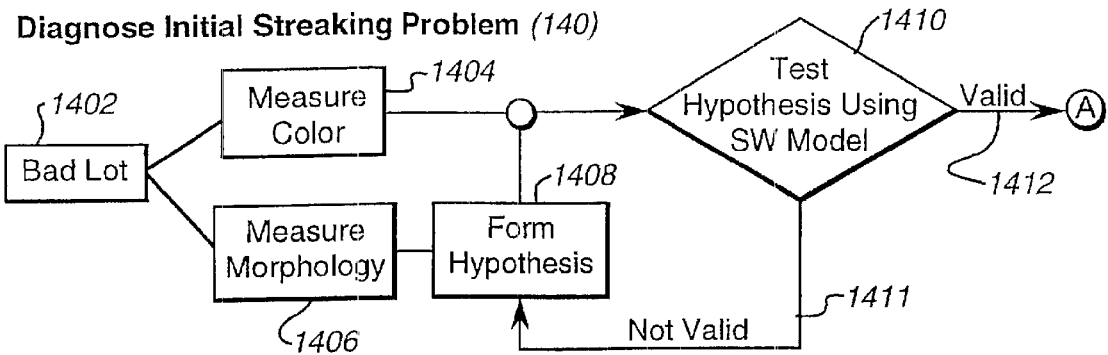
Replicate Problem on Lab (Small) Scale *(142)*
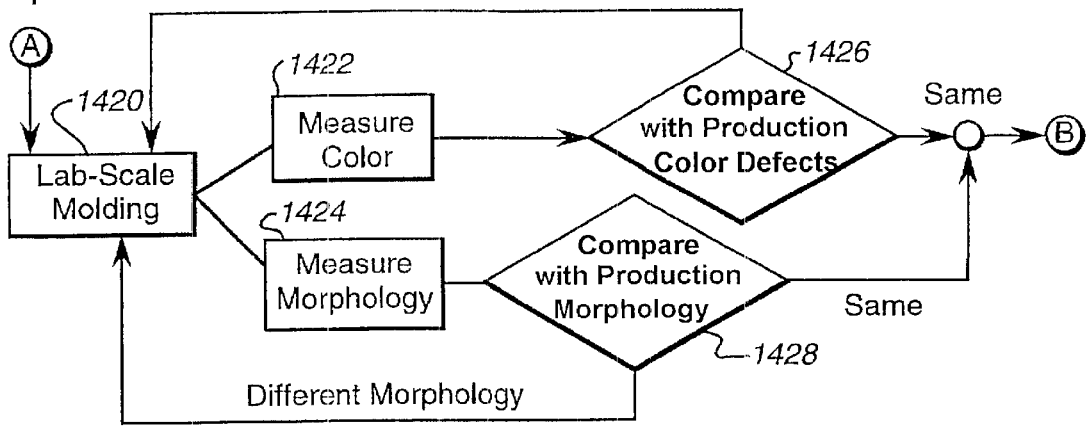
Determine and Test Corrective Procedure / Formula *(144)*
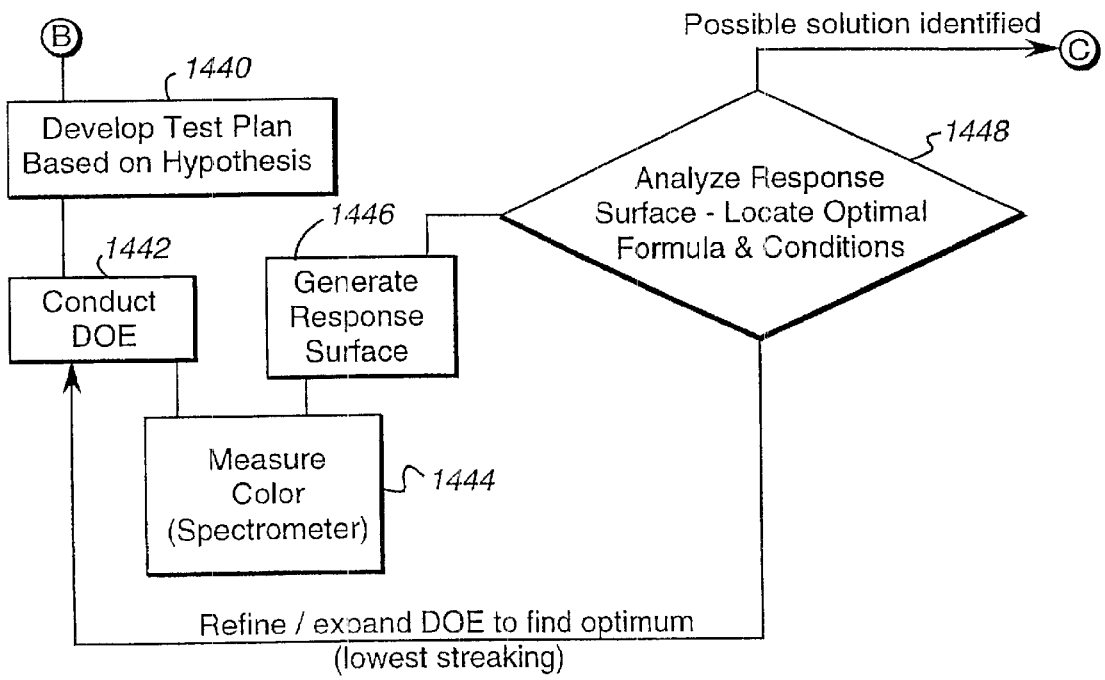
*fig. 14*

METHOD AND APPARATUS FOR RESIN FORMULATIONS WITH IMPROVED STREAKING PERFORMANCE

BACKGROUND OF THE INVENTION

This invention relates generally to correcting appearance variations in production-scale molded plastic parts, and specifically to using a laboratory-scale tool to duplicate streaking defects seen in production-scale parts and measuring and analyzing these defects so they can be corrected in subsequent production runs.

Consumers of durable plastic products ranging from toys to computer and printer housings to vehicles expect a uniform surface finish with no visible flaws, streaks, or defects. Common defects include streaks where various plastic flows meet in a part. These streaks may arise as different flow fronts from different gates meet or downstream of flow disruptions such as grills, bosses, ribs, or holes.

Currently, few, if any, numerical specifications related to uniformity of appearance are given to a supplier of raw plastic products outside of average color and possibly gloss or haze. Nevertheless, the molder creating the part and the consumer each expect a product with no visible flaws. The consumer, in particular, may view appearance defects as both unsightly and as indicative of poor quality material that will not last for long term use.

Currently, the quality, uniformity, and lack of defects in a part is typically judged solely using visual inspection on production parts. This leads to an absence of numerical specifications, lack of consistency due to operator variation, and an inability to consistently and rapidly process a large number of samples. Further, a large amount of waste may be generated since a large number of defective parts must be molded to attempt to quantify the problem. Often, the molder or customer is unable to transmit a complaint to the plastic supplier that is more specific than "a streaking problem exists," and many pounds of rejected production parts are shipped back to the plastic supplier for subsequent visual evaluation. Yet, it is difficult for the supplier to address the problem and provide solutions in the absence of effective measurement tools.

Several prior commonly-assigned and invented patents and patent applications, namely, U.S. Pat. No. 5,859,708, issued Jan. 12, 1999; and U.S. application Ser. Nos. 09/075,913; 09/188,094; and 09/188,095; address vagaries of visual inspection via a spatially resolved spectrometer which can resolve small defects which are not apparent to a standard spectrometer with the typical ½ inch diameter or larger aperture. Further, unlike the few spectrometers capable of smaller apertures which are not automated, the spectrometer described earlier may be interfaced with a computer for motorized sample movement and automatic data collection.

Commonly-assigned and invented U.S. patent application Ser. No. 09/303,409 discloses how to perform automated inspection of complex, curved, or textured parts, and how to process and quantify the massive amount of data generated by the spatially-resolved spectrometer of the above-references disclosures.

But, improving performance in production is still largely a "hit or miss" proposition, without quantitative information to guide the manufacturer.

Accordingly, there is a need in the art for a system and method to correct production defects by screening different resin formulations for streaking performance and to define processing windows which yield acceptable performance.

SUMMARY OF THE INVENTION

Using the molding tool, spatially-resolved spectrometer and computerized device of U.S. patent application Ser. No. 09/303,409, streaking problems identified in production are first duplicated on a laboratory scale. Next, options are developed for fixing (correcting) the observed problem and testing these on a laboratory scale. Finally, the option(s) chosen for correcting the observed problem are validated prior to reinitiating full-scale production.

Whereas the disclosure of U.S. Ser. No. 09/303,409 focuses on a molding tool, spatially-resolved spectrometer and computerized device and using these to establish appropriate resin formulations and processing conditions for a given production run with certain desired characteristics, the instant disclosure focuses on using the molding tool, spatially-resolved spectrometer and computerized device of U.S. Ser. No. 09/303,409 to analyze and correct preexisting production defects.

DETAILED DESCRIPTION OF THE INVENTION

The several commonly-invented and commonly-assigned issued and pending U.S. Patents noted earlier disclose a spatially-resolved spectroscopic tool for measuring visual characteristics of plastics, such as color, color blending, coining (e.g. scratching), etc.

This disclosure explains the use of the instrument and tools described in U.S. patent application Ser. No. 09/303,409 and Six Sigma methodology to produce resin formulations with vastly superior streaking performance to that previously available, particularly to duplicate and correct defects identified in molded plastic part production runs.

As disclosed in U.S. Ser. No. 09/303,409, the full system and method used to analyze streaking in molded plastic parts, according to one embodiment of that invention, comprises 3 parts: A molding tool that duplicates the streaking seen in real parts, the aforementioned spatially resolved spectrometer to measure color along the surface of the part, and post processing software to quantify the streaking. Various parts of the system may also be used alone, as appropriate. The system and method of U.S. Ser. No. 09/303, 409 will be largely reiterated below, to fully specify the tools and processes upon which the morphological characterization and correction of defects according to the present disclosure is based.

As used herein, the term "samples" will be used to refer to molded plastic parts produced by the molding tool according to the invention of U.S. Ser. No. 09/303,409, while "production" will be used to refer to a molded plastic part (such as a computer monitor housing, a printer housing, a television housing) that is the ultimate object to be produced using these analysis tools. In this context, the invention of U.S. Ser. No. 09/303,409 involves creating and using "sample" plastic parts to determine the optimum prescription for producing "production" plastic parts, so that defective production of production parts, and the cost and time for producing such production parts, is minimized.

Figure 1:
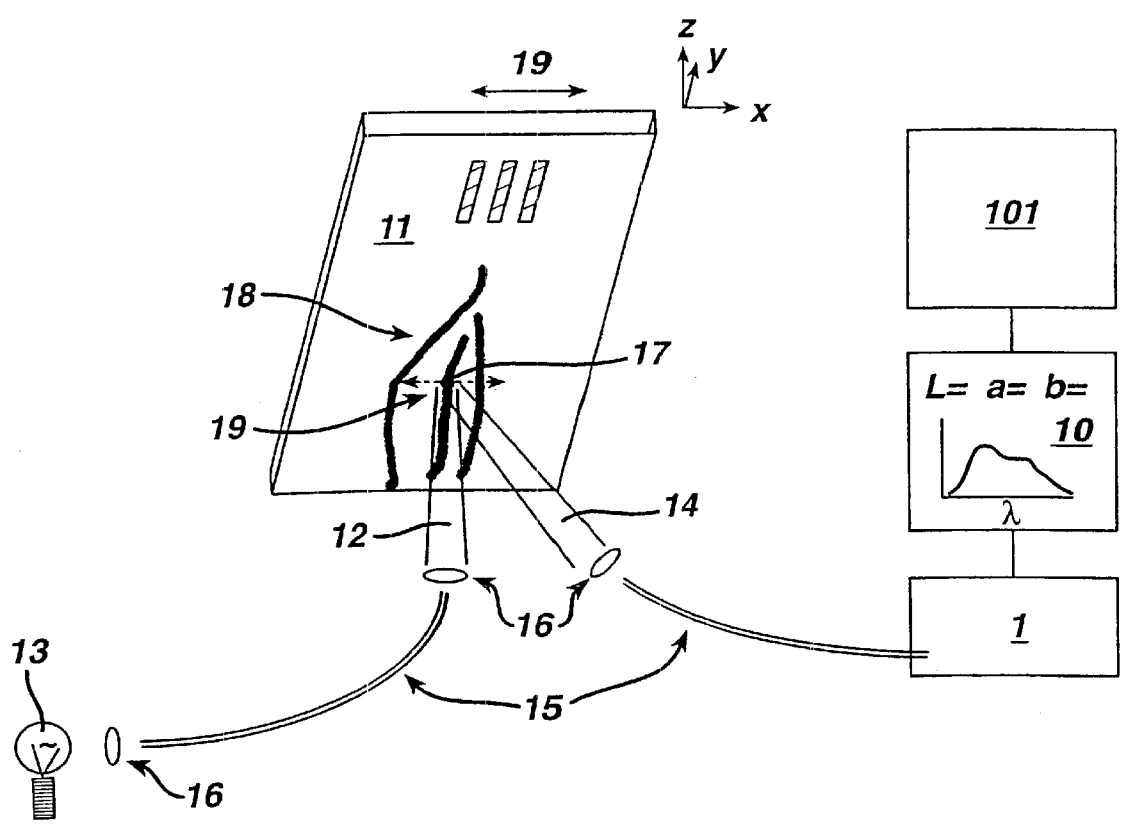
FIG. 1 is a schematic illustration of a spatially-resolved spectrometer for obtaining color readings from a plastic part being examined and analyzed.

As illustrated in FIG. 1., color measured by spatially-resolved spectrometer 1 is output in any conventional color format 10, such as but not limited to, CIELab units L, a, b. A molded plastic part 11 (which plastic part 11 may be a sample or a production part, but in this illustration is a sample) is evaluated by directing incident light 12 from a light source 13 onto plastic part 11 at a sample point 17, and reflected light 14 from sample point 17 is measured using spectrometer 1. Incident light 12 and reflected light 14 are carried to and from plastic part 11, for example, via light carriers 15 such as optical fibers, and are focused at sample point 17 as needed using focusing elements 16 such as one or more optical lenses. Incident light 12 may or may not be "focused" at sample point 17 in the scientific sense; so sample point 17 is simply to be understood as a point upon which light impinges 12 and is reflected 14. In order to evaluate streaking 18, plastic part 11 and sample point 17 are movable relative to one another in any direction along any combination of the x-y-z axes illustrated. A plurality of readings may thus be taken from different locations upon plastic part 11 at a plurality of locations spatially separated from one another by predetermined distances and directions. In this illustration, the samples are taken linearly 19 along the x axis. These readings are then input to the post-processing software for quantification and analysis. Molded plastic part 11, when it is a sample plastic part produced according to the invention of U.S. Ser. No. 09/303,409, will also sometimes be referred to as a "mold" or "plaque." The color format measurements 10 are then forwarded to a computerized device 101 for post processing as described in FIGS. 4 through 13.

In one embodiment of U.S. Ser. No. 09/303,409, spectrometer 1 and light carrier (e.g. fiber) couplings 15 are used in a 0–45 configuration, wherein incident light 12 impinges plastic part 11 at an angle of substantially zero degrees from perpendicular (i.e., normal to the plastic part 11 surface) and reflected light 14 is captured at an angle of substantially forty-five degrees from perpendicular. In other embodiments, incident light 12 angle is between zero and thirty, zero and forty five, and zero and eight-nine degrees from perpendicular. In other embodiments, reflected light 14 angle is between thirty and sixty, and between zero and eighty-nine degrees from perpendicular.

When a sample plastic part 11 is used, plastic part 11 may be mounted on a sample holder that is optionally mounted on motorized translation stages, so as to scan across the feature of interest. A computerized device (not shown) comprising computer software or hardware automates the motion system and data collection, and transforms the raw data into color coordinates. The computerized device guides the user through necessary calibration activities and allows the user to optimize the signal to noise by allowing adjustment of key parameters. Manual adjustment of the sample to selected locations is also possible, if desired.

Figure 2:
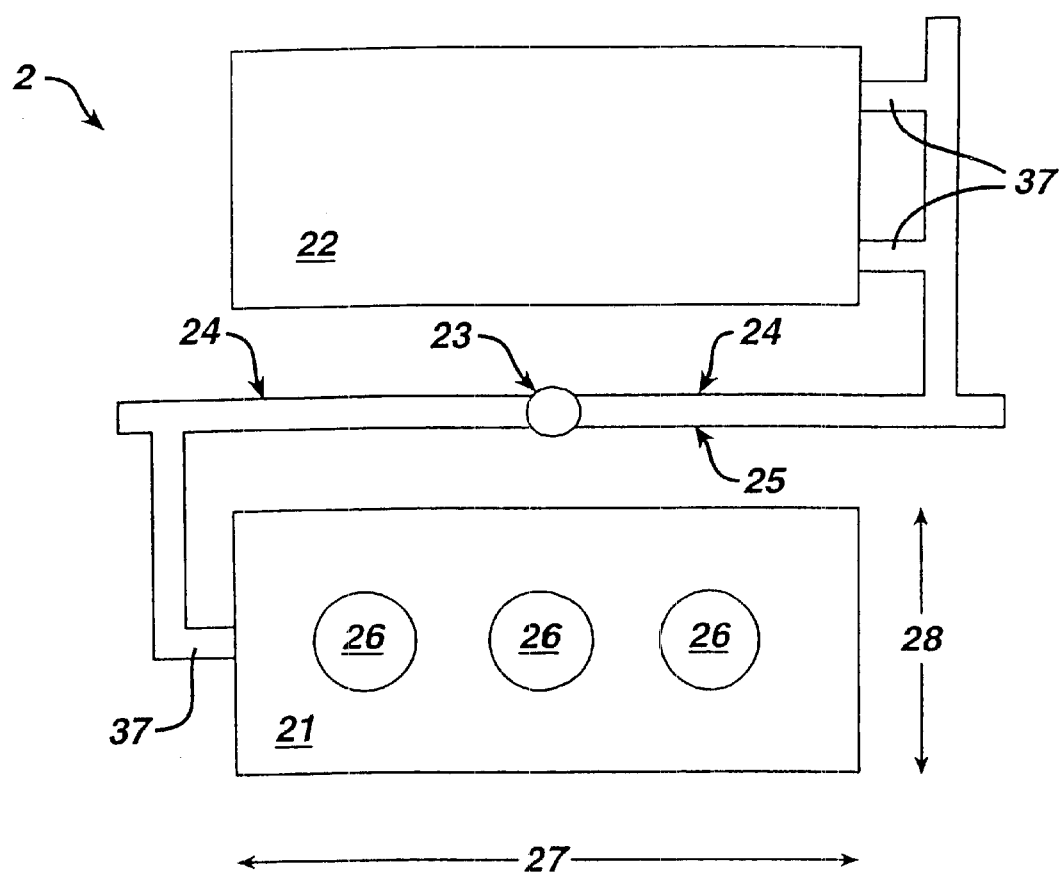
FIG. 2 is a plan view of a molding tool used to produce small-scale laboratory samples for analysis.
Figure 3:
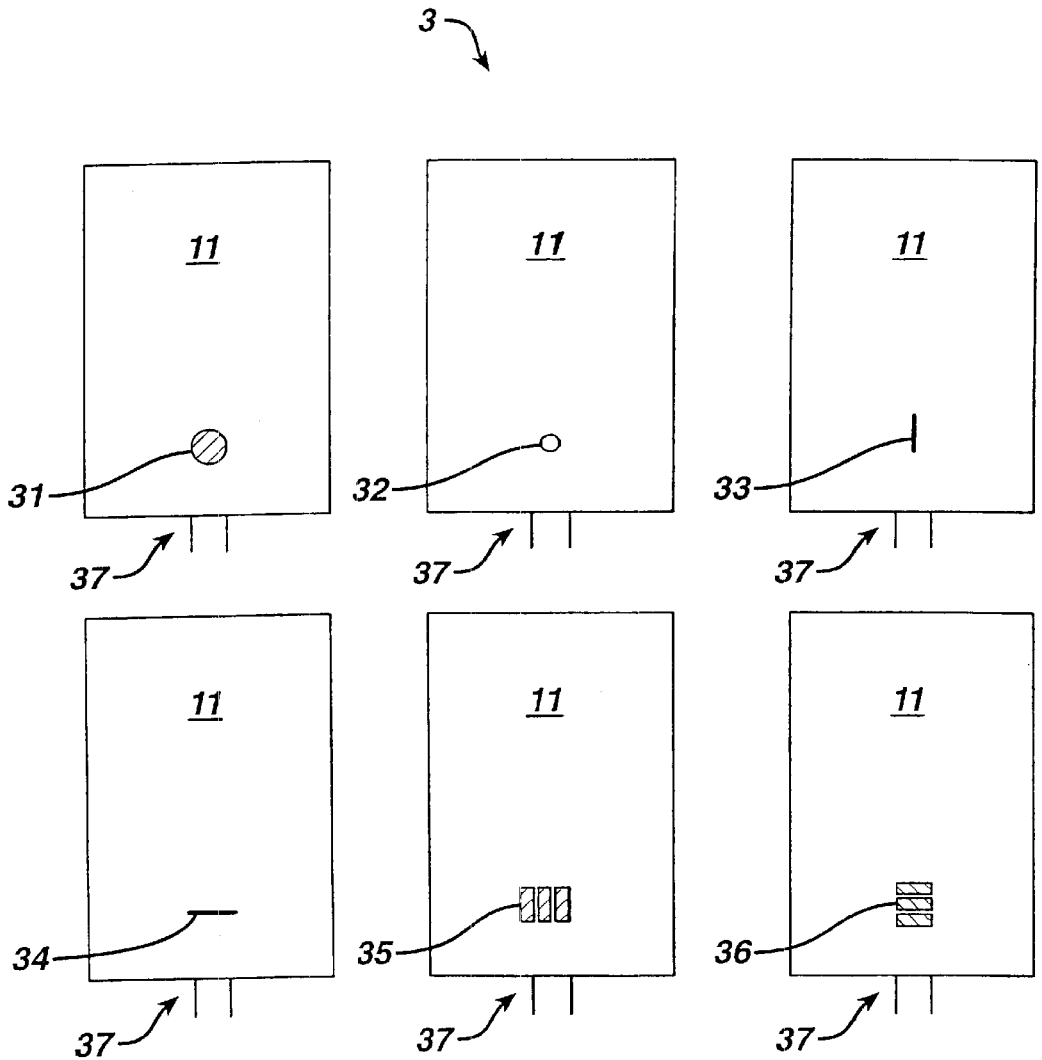
FIG. 3 is a plan view illustrating various mold configurations for use in connection with the molding tool of FIG. 2.

The molding tool, illustrated in FIGS. 2 and 3, comprises a system that allows the user to duplicate streaking from real parts on a laboratory scale. Samples produced in the molding tool are typically flat with a smooth, uniform surface finish, making them the ideal samples to be evaluated using the spatially resolved spectrometer.

A sample mold, such as a two-cavity molding tool 2 illustrated in the preferred embodiment of FIG. 2, comprises a single gate cavity 21 to produce single-gate plaques, and a double-gate cavity 22 used to produce double-gate plaques with knit lines. Extrusion of molten plastic from sprue 23 into one or both cavities 21 and 22 is controlled by valves at appropriate locations 24 in runner 25, and may be shut off or turned on as needed. A variety of inserts may then be placed into one or more insert receptacles to obstruct the flow (increase the chance to have streaking), for example, at any or all of the three different insert locations 26 in the single-gate cavity as shown. Molten plastic enters cavities 21 or 22 through gates 37.

While the dimensions can obviously be varied widely within the scope of the invention of U.S. Ser. No. 09/303, 409, cavity 21 and 22 have a preferred length 27 of approximately four to six inches, and typically about five inches, a preferred width 28 of approximately two to four inches, and typically about three inches, and a preferred thickness (not shown) of approximately $\frac{1}{32}$ to $\frac{1}{8}$ inch, and typically about $\frac{1}{16}$ inch. The goal is to have small-scale, easily molded and handled samples, which have a smooth, flat surface finish for best evaluation using the spectrometer. Thus, any particular size and thickness may be chosen within the scope of the invention of U.S. Ser. No. 09/303,409 which best duplicates the results seen in production samples on a smaller scale, even outside the ranges enumerated above. Thickness, in particular, may depend on plastic formulation, properties such as melt temperature and viscosity, and final production part thickness. Insofar as weight in concerned, a Cycoloy C6200 part and runner, for example, weighs approximately 1.2 oz (33 g). While the Cycoloy C6200 is used for a specific plastic formulation, any formulation of interest could be used for producing sample plastic parts according to the invention of U.S. Ser. No. 09/303,409. The weights would generally be similar for different plastic formulations.

FIG. 3 illustrates various sample plastic part (plaque) 11 configurations that can be produced utilizing various mold inserts in connection with the molding tool of FIG. 2. In particular, a plurality of molding tool inserts are inserted into one or more of the insert location 26 of molding tool 2. Each such insert is designed to produce, for example, molds (plaques) 11 with a "hole" 31, "boss" 32, "rib" parallel to the plastic flow 33, "rib" across the plastic flow 34, "grill" parallel to the plastic flow 35, and "grill" across the plastic flow 36. The configurations illustrated in FIG. 3 are produced by placing a single "topological" insert into the insert location 26 closest to gate 37 of single gate cavity 21, and a pair of "blank" inserts into the remaining two insert location 26 of single gate cavity 21. Thus, the molding tool inserts are illustrated in terms of the "negative" of the surface features 31, 32, 33, 34, 35, 36 illustrated in FIG. 3.

It is understood therefor, that reference to, for example, a "boss" insert 32 refers to an insert that when inserted into single gate cavity 21, and after molten plastic is extruded into single gate cavity 21, will produce the topological surface feature illustrated by 32. Similarly, general references to molding tool inserts 3, will be understood to refer to molding tool inserts that embody the negatives of, and produce surface features such as, those illustrated in connection with the six plaques 11 of FIG. 3.

The six particular configurations illustrated in FIG. 3 are typical of the "topological" surface features commonly encountered in "production" plastic moldings, and so enable "sample" moldings to be produced that have surface features that will be produced in the production moldings for the planned production runs. Of course, these are just examples of the types of configurations that can be produced by the inserts, and it is understood that molding tool inserts 3 that are designed to produce additional surface features not expressly illustrated in FIG. 3 may also be developed and used according to the invention of U.S. Ser. No. 09/303,409. Also, the ribs and grills (and any other surface features produced by other insert types that are not radially symmetric) can be oriented at any angle relative to the main flow through gate 37. Similarly, while double gate cavity 22 utilizes two gates 37 with substantially parallel input, it is understood that any number of gates can be used, with varying relative orientations to one another, in accordance with the invention of U.S. Ser. No. 09/303,409.

Thus, in use, if it is known that a "production" plastic part to be manufactured is to have certain topological features, either separately or in combination, "topological" molding tool inserts 3 are placed into one or more of the insert locations 26, and "blank" inserts are placed into any remaining insert locations 26. Then, molten plastic is extruded into single gate cavity 21 or double-gate cavity 22 via gates 37. (Double-gate cavity 22 may be used where it is known that the production plastic part will be produced by double gate injection.) The plastic is allowed to harden, and the resulting plaque(s), with surface features such as 31–36, and with double-gate injection features if pertinent, are removed and placed under spatially-resolved spectrometer 1 as earlier described in connection with FIG. 1. The streaking 18 resulting from the topological feature or features of interest (or from double gate if double-gate cavity 22 is used) is then analyzed by spectrometer 1 as discussed below. It is to be noted that the plaque 11 used as an example in the illustration of FIG. 1 is one with a "grill" parallel to the plastic flow 35.

As detailed below in the discussion of FIGS. 4 through 13, post processing using a computerized device comprising hardware or software in appropriate combination, reduces noise by smoothing the raw color scans and calculates the difference in L values (using CIELab color space) between the lightest and darkest points across a streaked region. That is, if a dark line is observed down the part, it is desirable to look at the "normal" color on either side of the line as well as the variation from one "normal" region to the other across the discoloration. Various embodiments are possible. For single-streak parts, Delta L or area under the curve may be calculated. For parts with multiple streaks, the values for each streak may be averaged or the values for each streak may be reported individually. The user may also choose to view either the raw data or the smoothed data with no further post processing. While the invention of U.S. Ser. No. 09/303,409 is described with reference to CIELab color space, it is understood that any other means of characterizing and analyzing color can also be used in accordance with that invention.

Once a number of molded plastic part samples have been produced and each has been scanned by spatially-resolved spectrometer 1 according to the invention of U.S. Ser. No. 09/303,409 as described in reference to FIGS. 1 through 3, it is desirable to compare the various samples and determine which sample has the optimum appearance. This in turn makes it possible to determine which mix of ingredients and which set of processing conditions should be used in production.

There are three primary types of data that are made available for this purpose according to the invention of U.S. Ser. No. 09/303,409. First, since the slopes of the peak and valley curves represent how rapidly color variations take place from one space to the next in any given sample, and since smoother (lower slope) variations are preferred to sharper (higher slope) variations, it is desirable to obtain a "quality" measurement based on these slopes. Second, it is desirable to obtain a detailed description of the overall shape characteristics of the appearance of the sample. Finally, one measure of the desirability of any given sample is based on height variation from each peak to the adjacent valley, as well as on an overall average of these. In all cases, since there will be statistically insignificant color variations measured from one linear position to the next for any given sample, it is desirable prior to performing any of these calculations to filter out these insignificant variations to obtain a plotting of true peaks and valleys, over the space being considered, for each sample.

Figure 4:
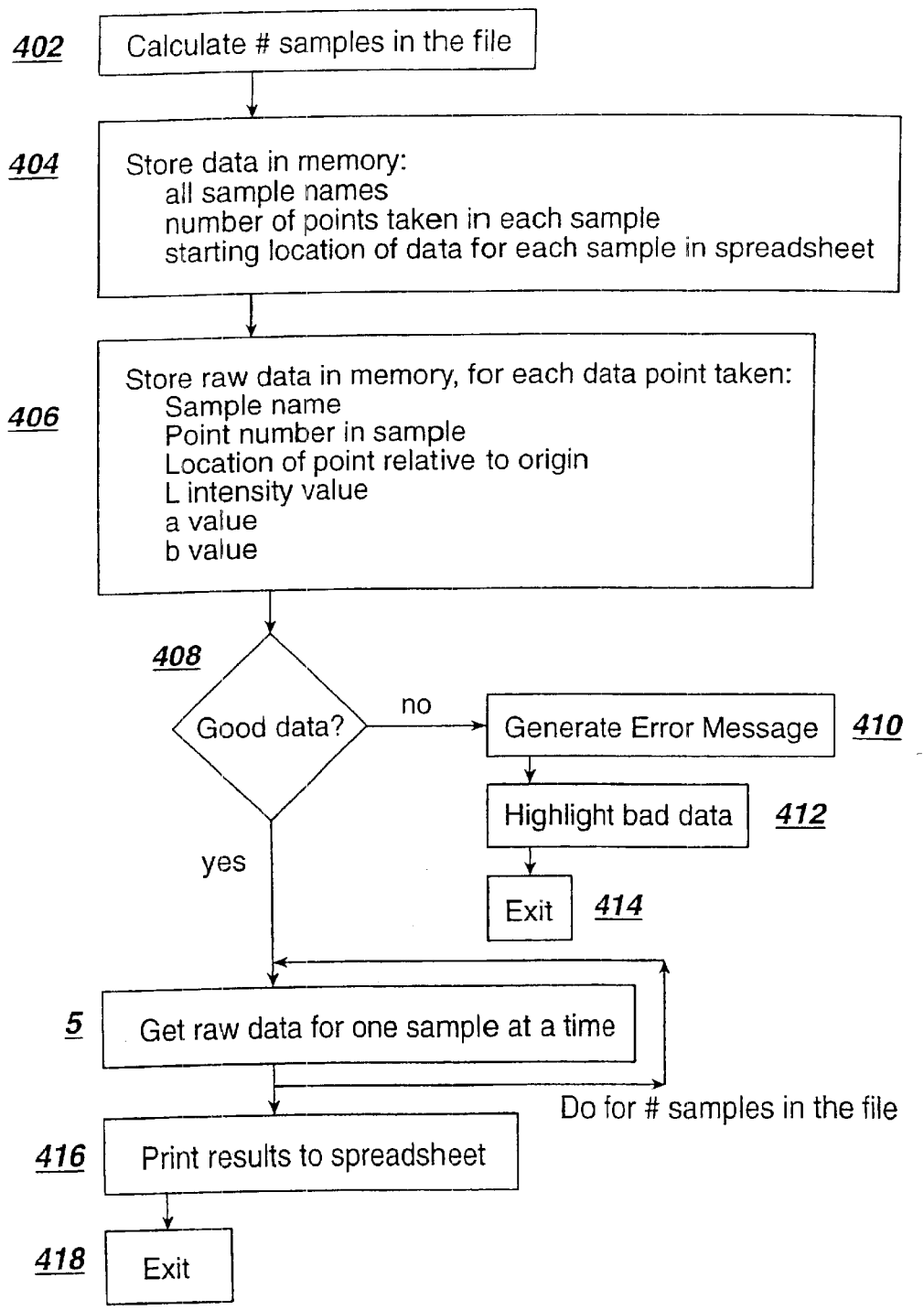
FIGS. 4 and 5 are flowcharts illustrating methods of post-processing color readings from the spatially-resolved spectrometer of FIG. 1.
Figure 5:
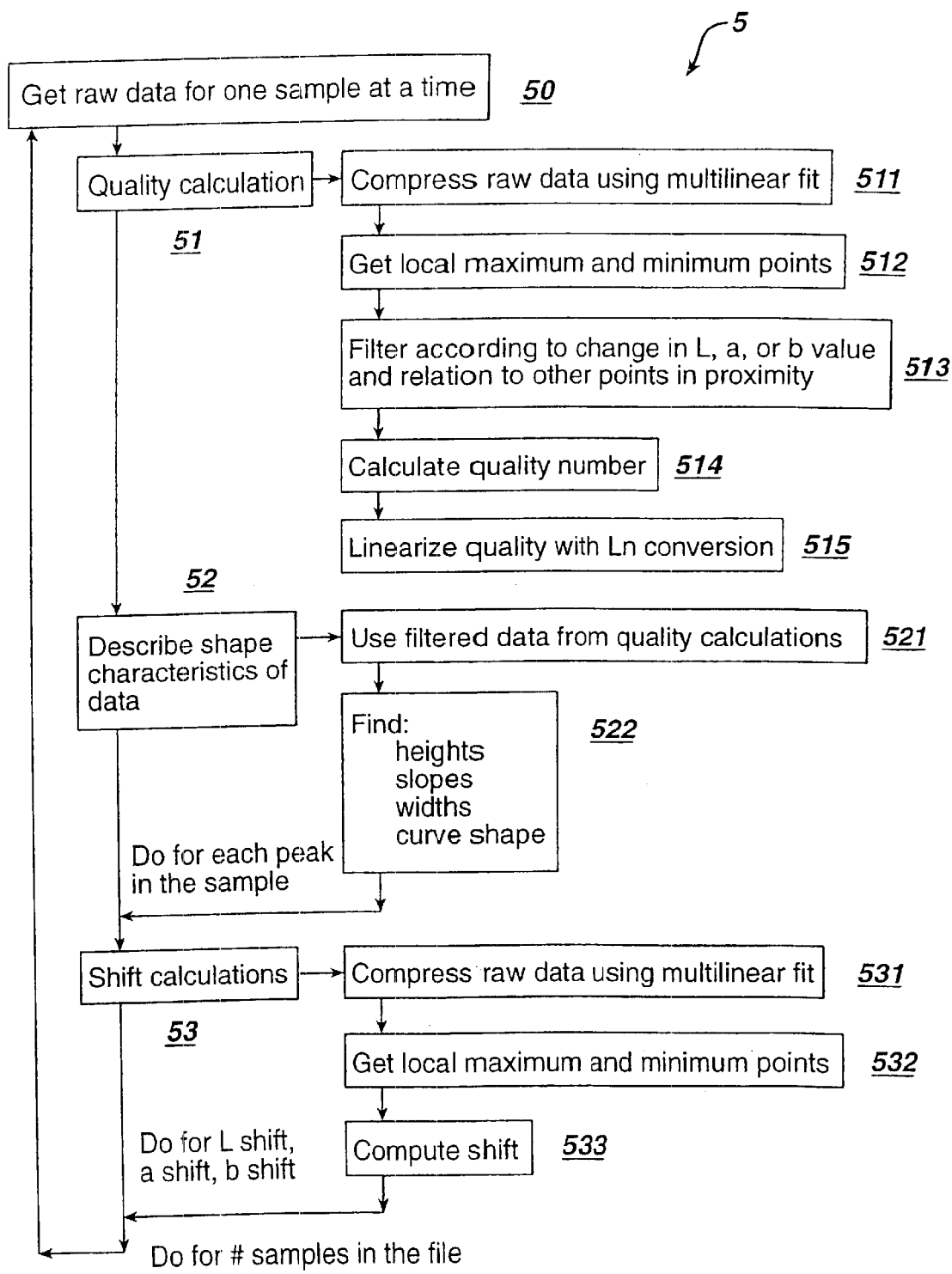

FIGS. 4 and 5 are flowcharts illustrating this overall calculation process. At 402, computerized device 101 first determines the overall number of plastic part samples 11 that have been scanned for analysis. In the discussion to follow, the term "sample" or "sample data" will generally be used to refer to the overall set of CIELab (or similar measure) color data points obtained by the process outlined in FIGS. 1 through 3, for each plastic part sample. For example, if a dozen plastic part samples were produced and scanned, there would be twelve sets of sample data associated with these twelve part samples, and each data sample would contain a number of data points. At 404, names or similar identifiers associated with each sample are established, along with the number of data points for each sample. The first data point for each sample is similarly identified. At 406, each data point is stored in the computerized device with several associated pieces of information, including the sample name or identifier, the number of that particular point in the overall sample, the spatial position of that point relative to the origin (i.e., the first data point for that sample), and the L, a and b values. At 408, the data is examined for completeness. It is determined if all required data fields are present (sample name or identifier, point number in sample, spatial location on sample, L, a, b) and if the numerical fields (all but the name) are numerical. From 408, incomplete raw data is eliminated at 410, 412 and 414, while complete raw data is then analyzed for one sample at a time at 5, using the process summarized below in connection with FIG. 5, until the analysis is complete for all samples. The results are then output at 416 to a suitable data output device such as a spreadsheet, computer display monitor, printer, etc. in a suitable data format such as numeric data, graphical representation, etc. The process concludes at 418.

In FIG. 5, which comprises step 5 of FIG. 4 and illustrates the overall processing of data for a single sample, computerized device 101 first obtains the raw data for the given sample at 50. Then the first of the three above-referenced calculations—the quality calculation 51—begins.

Figure 6:
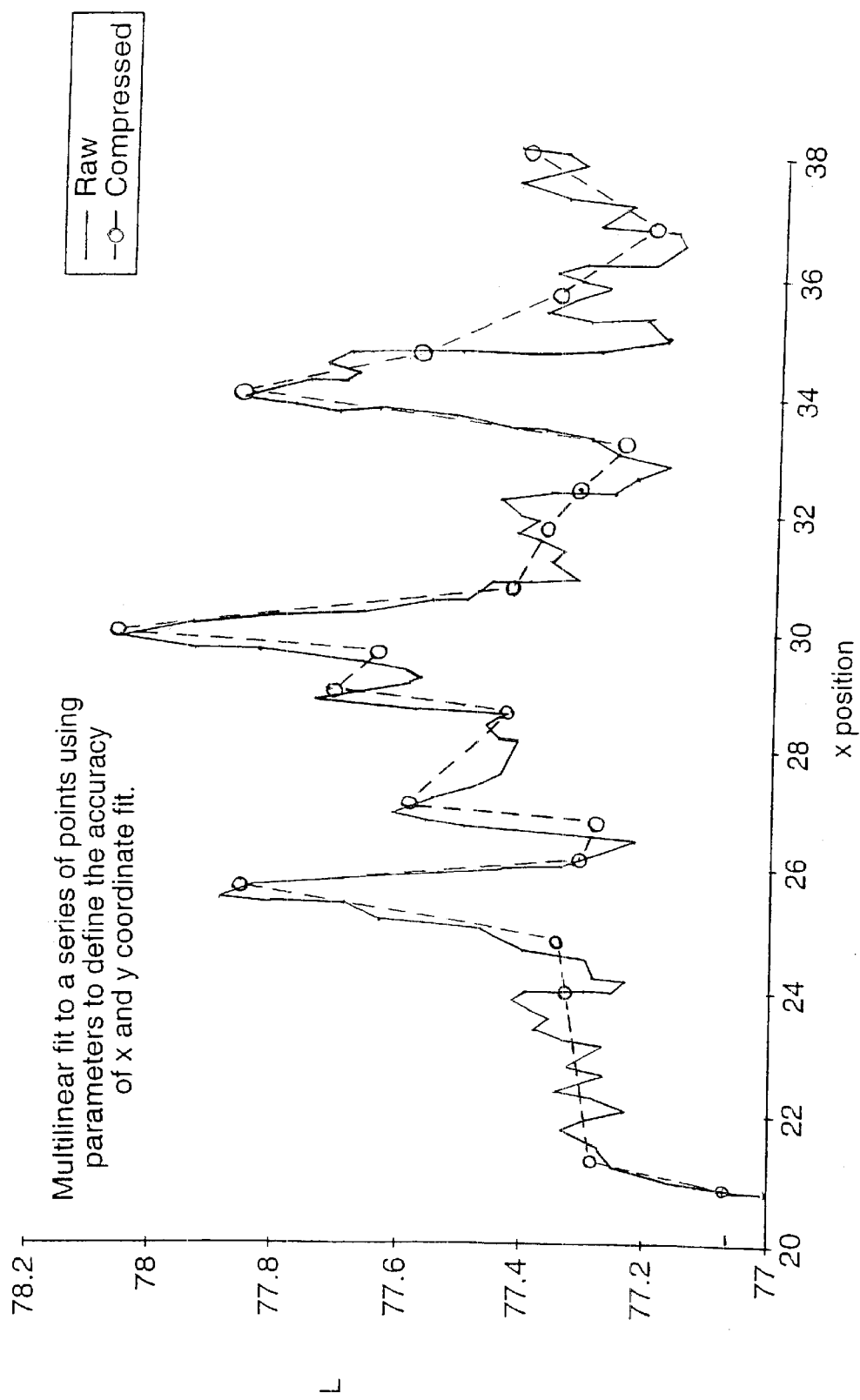
FIGS. 6 through 9 illustrate sample data representative of color signal shape including peaks and valleys, as that data undergoes several iterations of post processing filtering.
Figure 7:
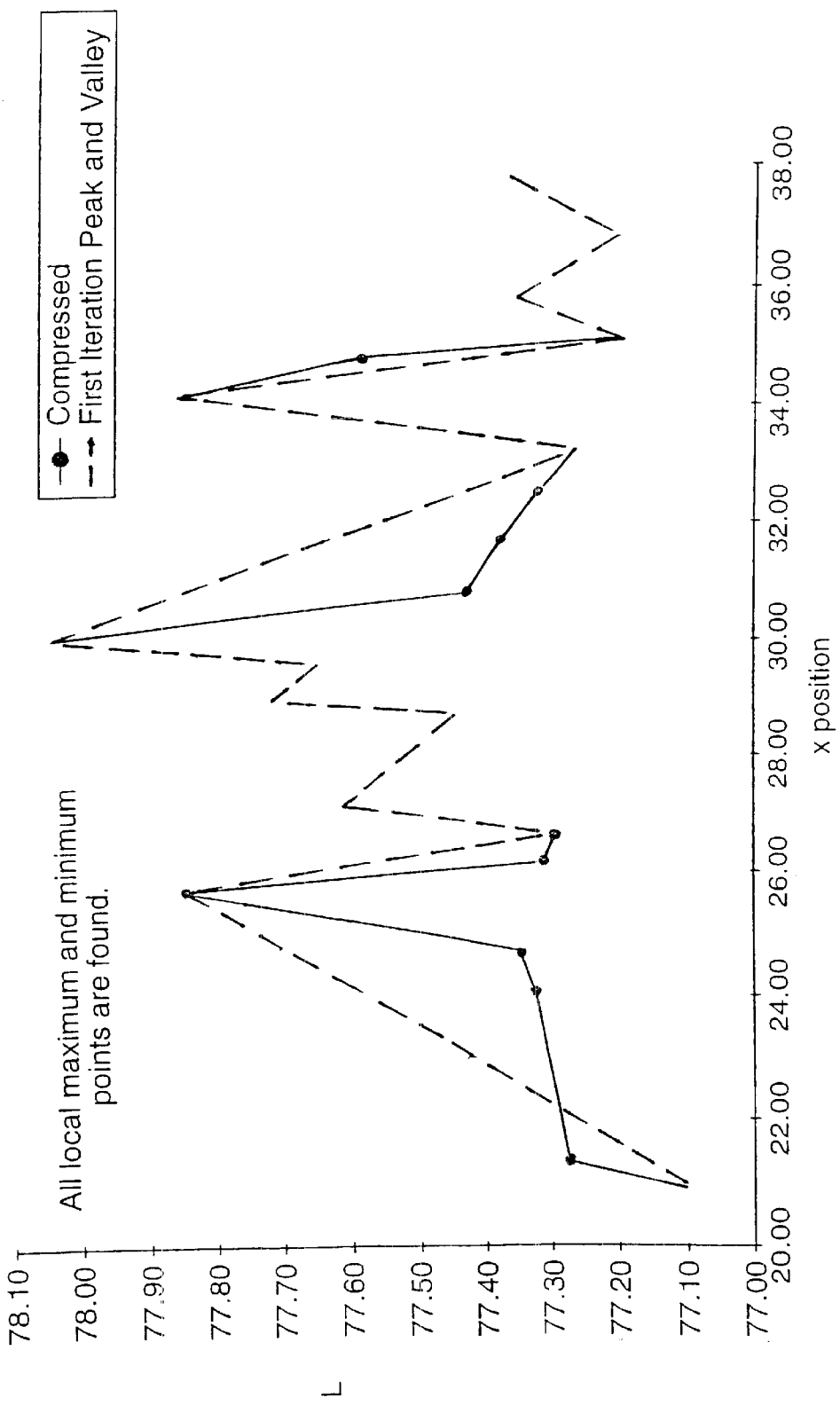
Figure 8:
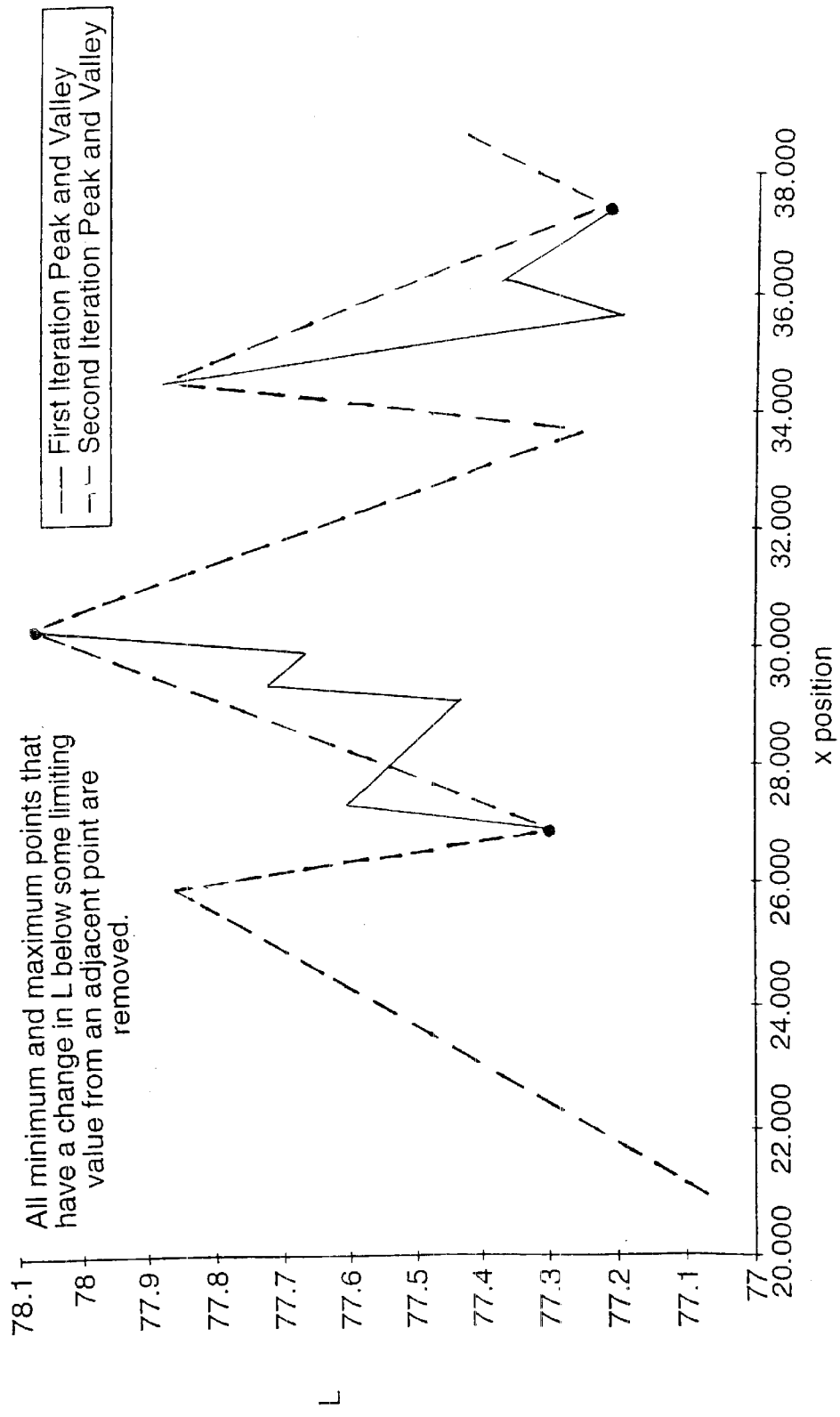
Figure 9:
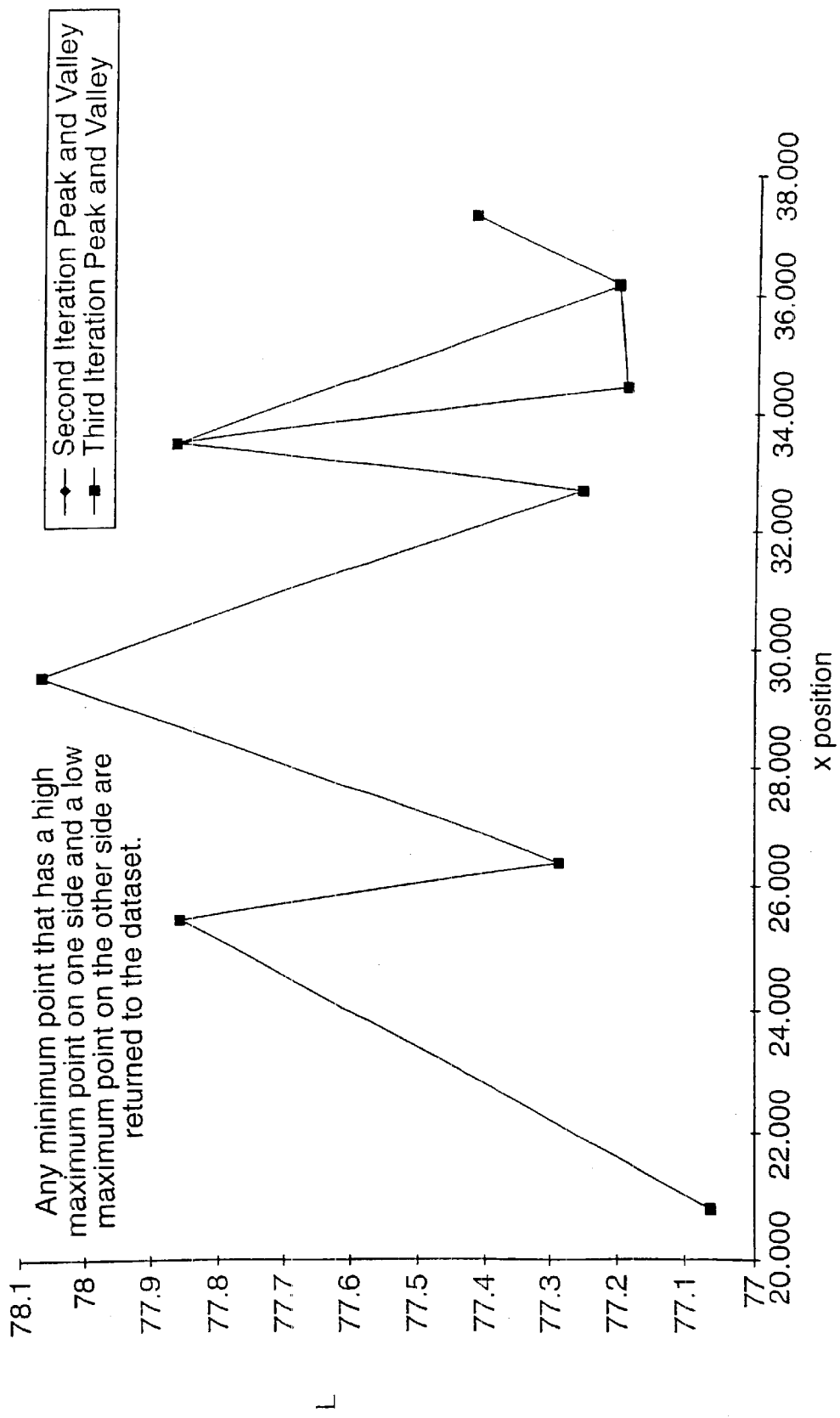

At 511, small fluctuations in L, a, b indiscernible to the human eye are filtered out, using a multilinear fit to a series of points using parameters to define the accuracy of the x and y coordinate fit. As illustrated in FIG. 6, local "noise" in the raw data is filtered out, and only variations above certain predefined threshold parameters are maintained. This results in the "compressed" data plot superimposed over the corresponding "raw" data plot in FIG. 6. At 512 and 513, this compressed data is then further filtered through several iterations (in this example, three) illustrated in FIGS. 7, 8 and 9. The first iteration at 512 (FIG. 7) identifies all local extreme, i.e., maximum and minimum, points. Detecting local minimum and maximum values allows determination of defects or inconsistencies in the sample such as "streaking." The second iteration at 513 (FIG. 8) removes from the data set, all minima and maxima with a change in L (or a and b for those calculations) from the adjacent minima and maxima below a predetermined limiting value, so that only significant variations are maintained. The third and final iteration, also at 513 (FIG. 9) then returns to the data set any minimum point that has a high maximum point on one side and a low maximum point on the other side. The data output from 513, illustrated by the example in FIG. 9, will be henceforth referred to as (final iteration) "filtered" data. Fluctuations in L, a, and b values following this filtering indicate changes in the appearance of the sample.

Figure 10:
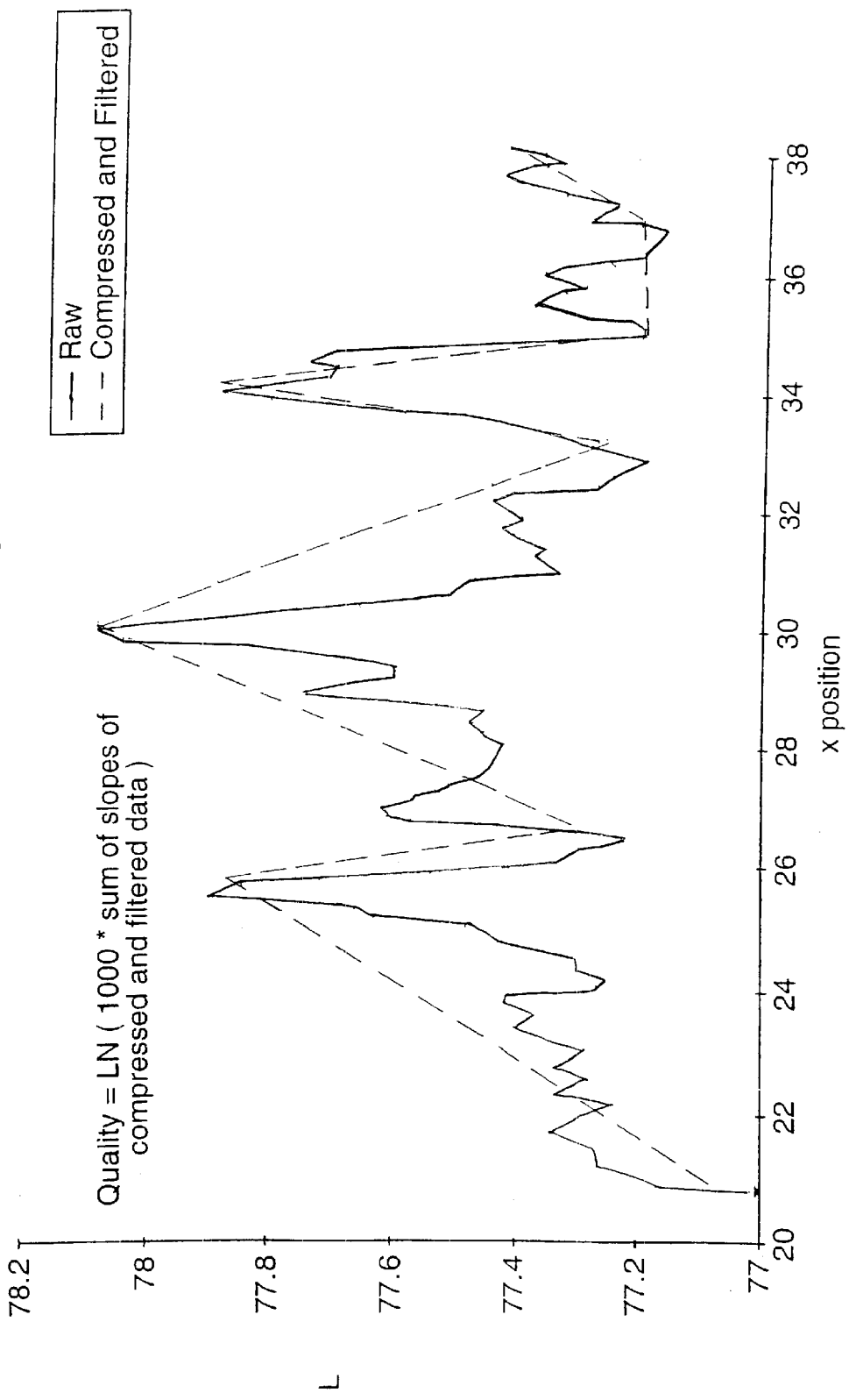
FIG. 10 illustrates the method used to calculate a quality measure of the sample under consideration, from the sample data of FIGS. 6–9.

Next, a quality number is calculated at 514. The Quality number is a way of ranking the samples according to the number of streaks apparent and the signal intensity shift. It is linearized 515 so that ranking of several test samples is scaled correctly. FIG. 10 illustrates a sample calculation of this quality number. If Q=quality number, $\Sigma dL/dx$=the sum of the slopes of the filtered data from 513, and M=a suitable multiplier such as 1000, then:

$$Q = ln(M * \Sigma DL/dx) \qquad (1)$$

Similarly, for a and b data, once simply substitutes a and b for L in the above. By its relation to the first derivative (slope) of the L, a and b curves, Q essentially measures the smoothness or sharpness of any measured streaking. As noted above, this is the first of the three primary measures used to determine which among all samples is to be used as the basis for a full-scale production recipe.

Figure 11:
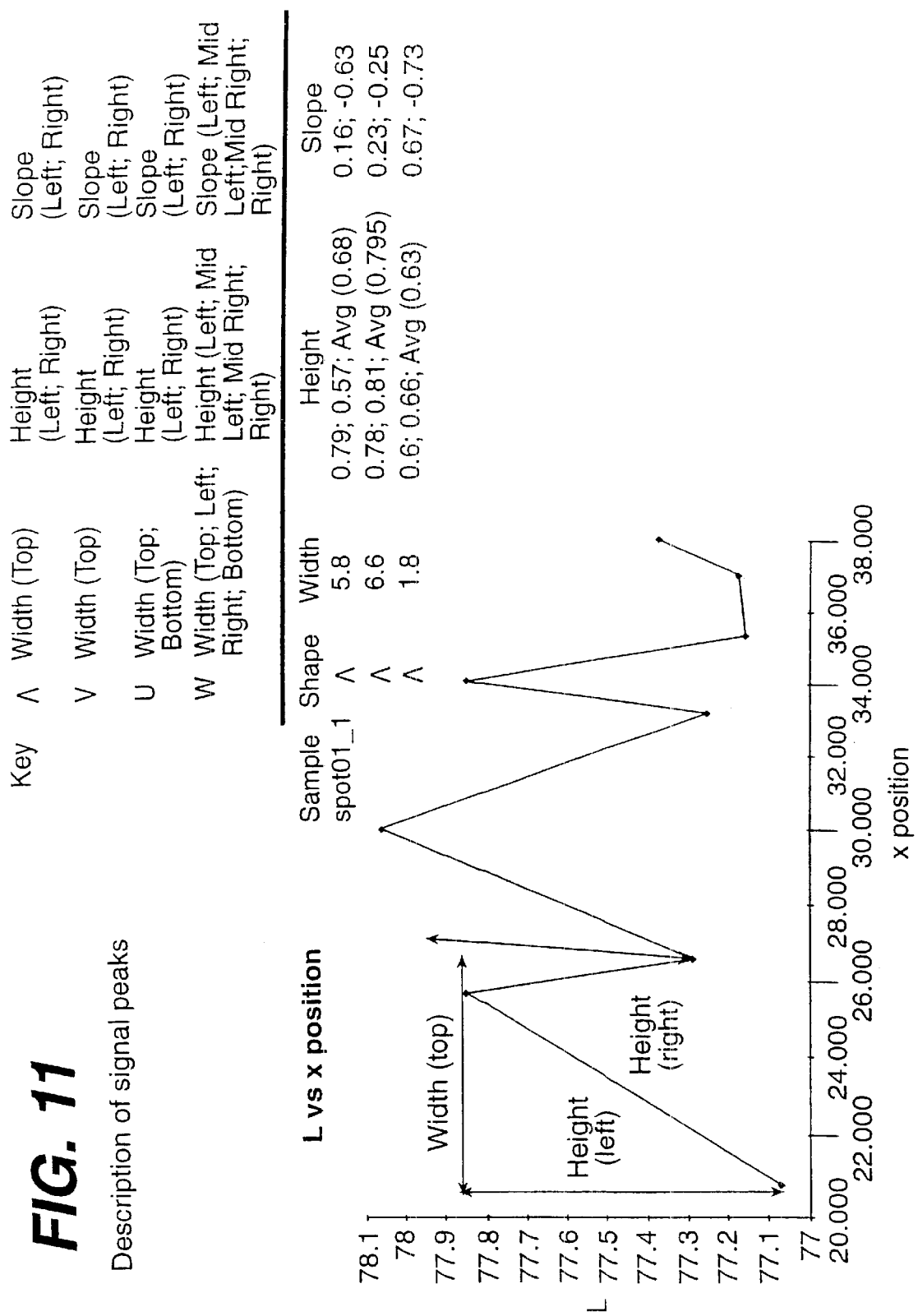
FIG. 11 illustrates the method used to describe the shape of the sample data of FIGS. 6–9.
Figure 12:
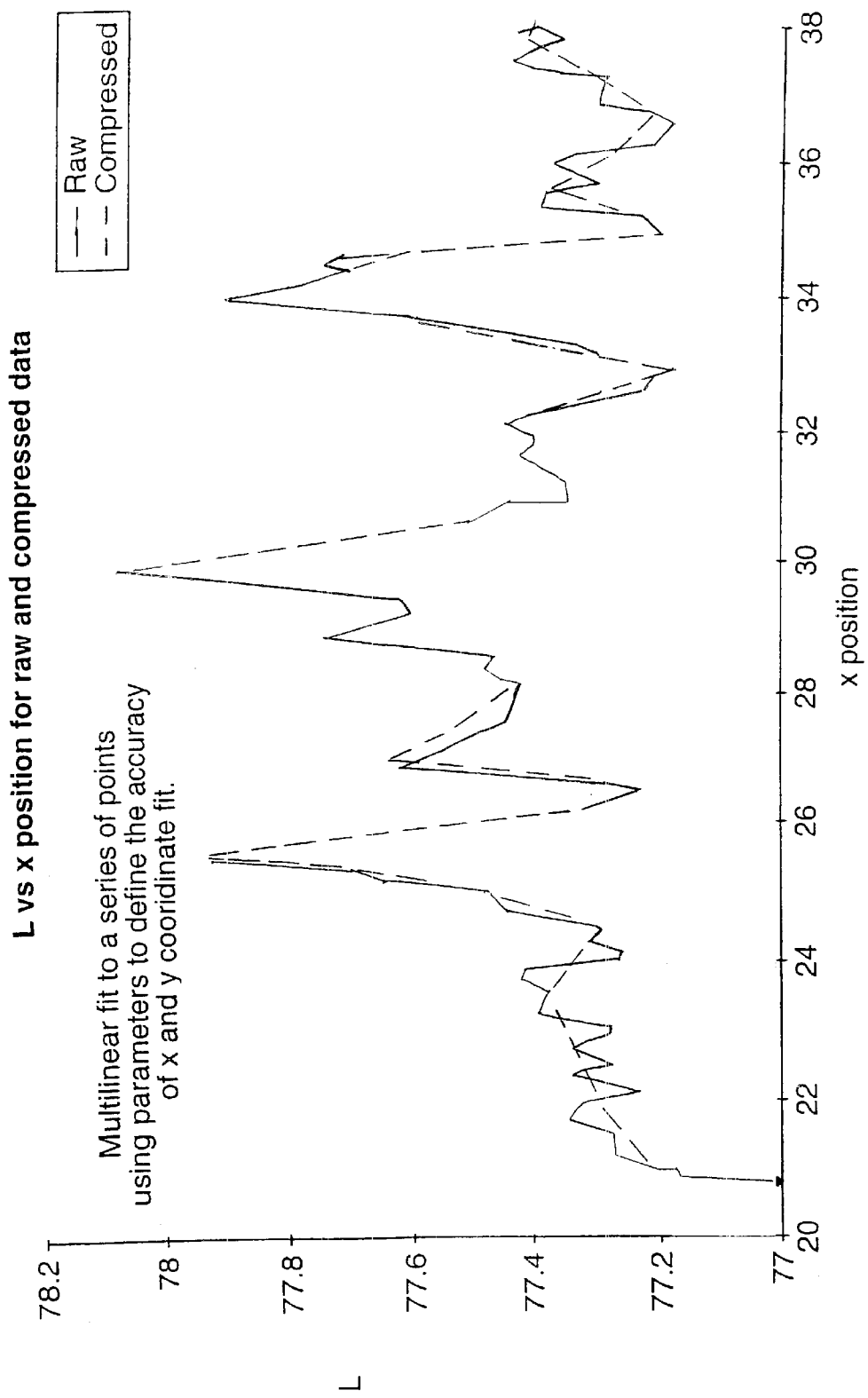
FIGS. 12 and 13 illustrate the method used to average the degree of variation from peak to valley over the entire sample, using the sample raw data of FIG. 6.

Next, at 52, the overall shape characteristics of the data are described, using the same filtered data from 513 (illustrated in FIG. 9) that was used to calculate quality number Q. Using this filtered data at 521, one arrives at a clear representation of signal peaks that can then be quantified in various ways as shown in FIG. 11. Data taken from various samples in fact shows that different types of defects give different looking peak shapes.

At 522, descriptive data such as height, slope, width, and curve shape allows the user to quantify and qualitatively describe the difference between samples. The number of defects in a sample as well as the signal intensity of each individual defect are important to the user. This is the second of the three primary measures used to determine which among all samples is to be used as the basis for a full-scale production recipe. Some example width, height and slope data resulting from shape analysis 52 are illustrated toward the upper right of FIG. 11.

Figure 13:
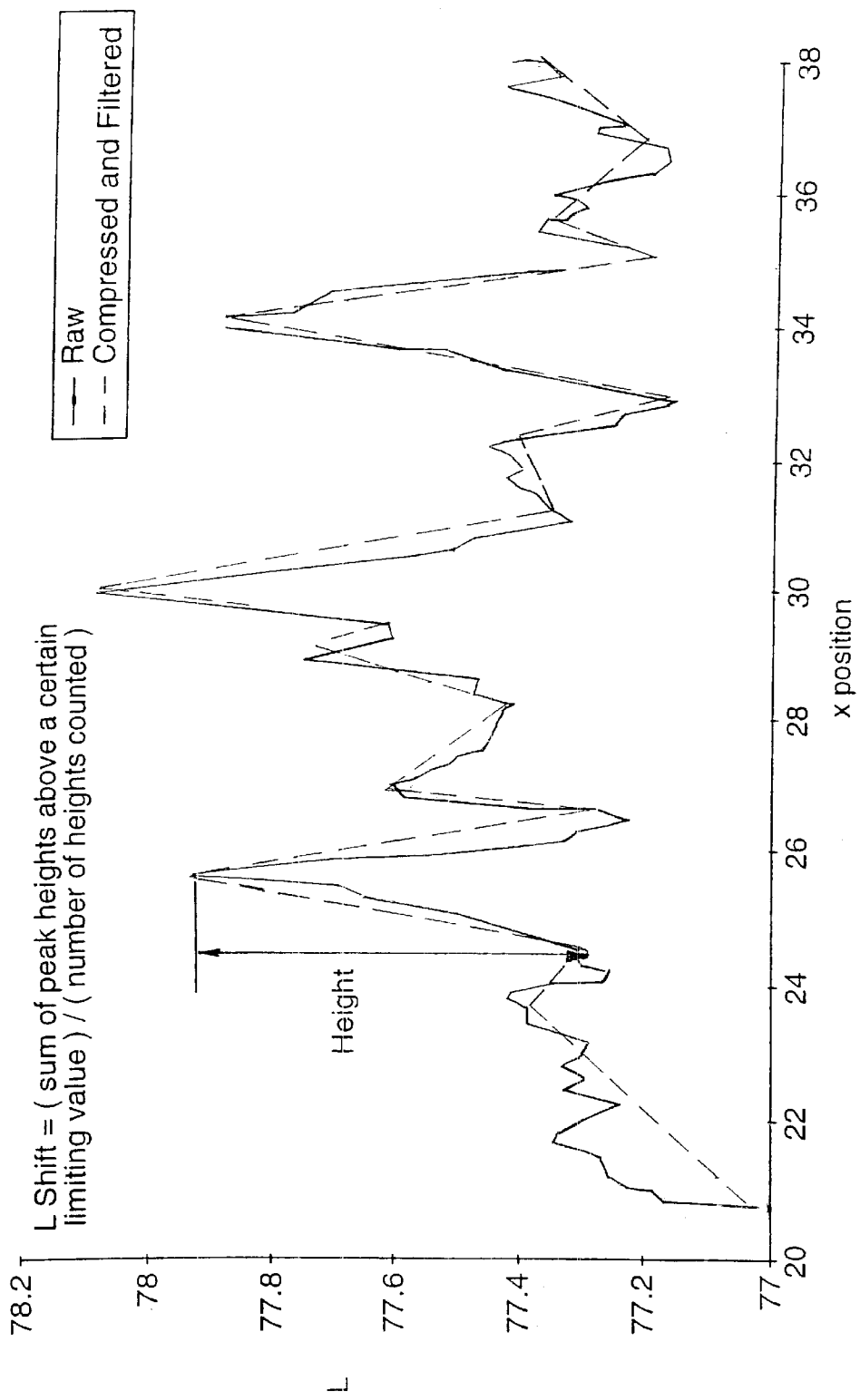

Finally, L, a, and b shift calculations are performed at 53 to describe the signal intensity shift and color shift across the sample taken. Whereas quality calculation 51 and shape analysis 52 share the same compressed 511 and filtered 513, 521 data, shift calculation 53 in the preferred embodiment does not. At 531, local "noise" in the raw data is filtered out, and only variations above certain predefined threshold parameters are maintained, resulting in a second compressed data set similar to that obtained in 511. However, it is generally preferred to use a different set of threshold parameters for shift calculations 53 than for quality 51 and shape 52 calculations and analysis. Similarly to 512, local maximum and minimum points are again obtained 532, but again, these are based on the preferably different threshold parameters used at 531. The three filtering iterations 513 are not performed. Then, at 533, the shift is computed. FIG. 13 illustrates this for a sample L shift calculation. Peaks below a certain predetermined threshold height are then discarded, and the L shift, as well as a and b shifts, are calculated from peaks above that predetermined threshold 512. If S=shift, T=total sum of peak heights above threshold, and N=number of peak heights above threshold, then $$S = T/N. \qquad (2)$$

That is, the shift simply measures the average peak height of a given sample, which as noted earlier, is the third of the three primary measures used to determine which among all samples is the be used as the basis for a full-scale production recipe. If desired, the individual shifts may be reported rather than the average.

It is understood that FIGS. 6 through 13 illustrate graphical representations of numeric data stored in and operated upon by computerized device 101, and of course, that FIGS. 6 through 13 are simply illustrative of the invention of U.S. Ser. No. 09/303,409 and not limiting. It is further understood that this numeric data, including numeric data indicative of such features as coordinates, slopes, shapes, etc., can be represented within computerized device 101 in a wide variety of ways that would be apparent to someone of ordinary skill. Finally, it is understood that specific any manner of representing the numeric data underlying FIGS. 6 through 13 in computerized device 101 using practices common in the art is considered to be within the scope of the invention of U.S. Ser. No. 09/303,409 and the claims associated therewith.

This system may be used to quantify all manner of appearance defects, including light and dark streaks. With further refinements and software optimization, it could be used to evaluate splay, surface defects (gloss or roughness), and others.

Figure 14:
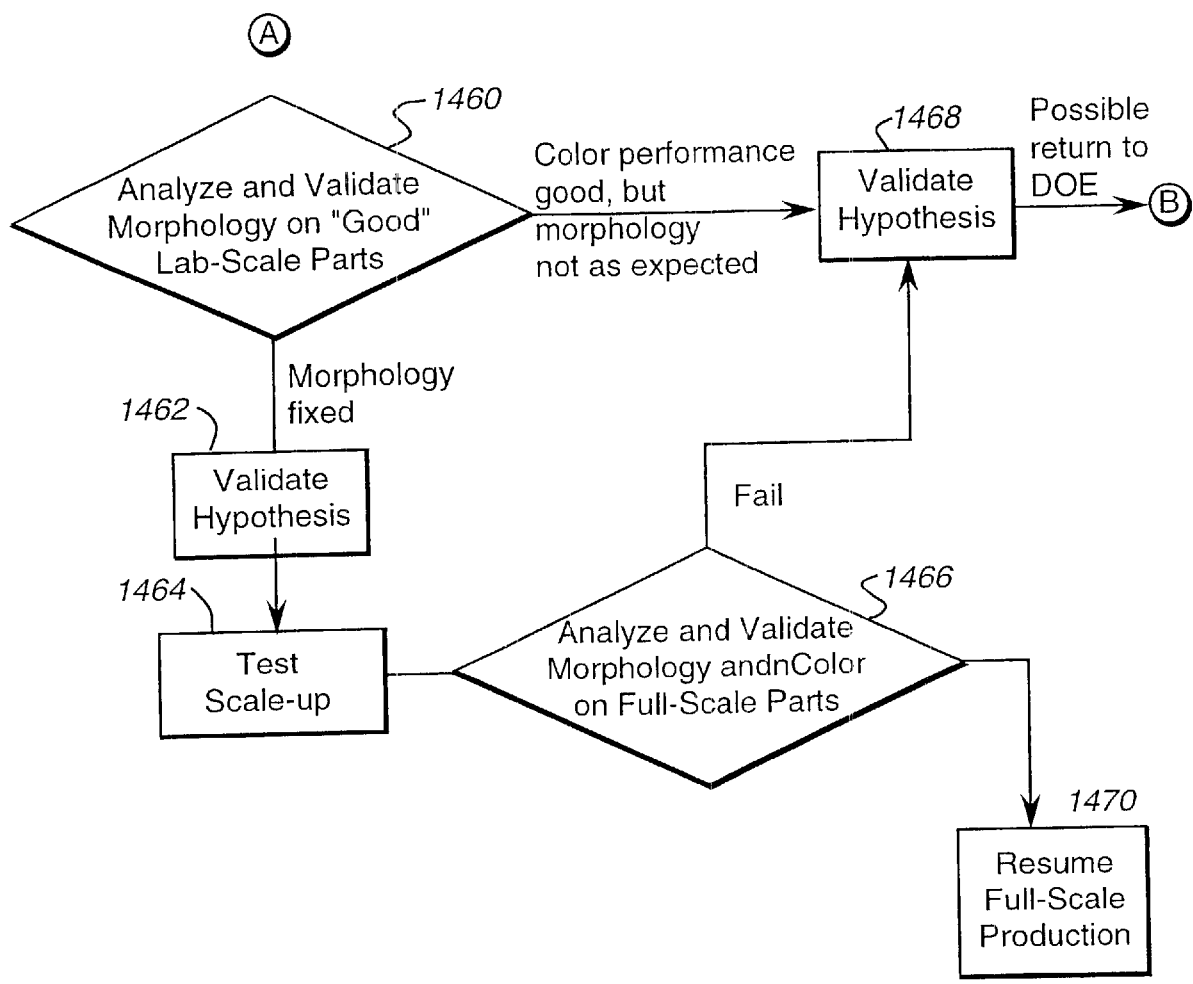
FIG. 14 is a flowchart illustrating an embodiment of the present invention to correct defects observed in full-scale plastic part production.

According to an embodiment of the present invention, the four main steps by which the tools and methods of U.S. Ser. No. 09/303,409 are used to correct defects observed in full-scale plastic part production are to 1) diagnose the initial streaking problem, 140; 2) duplicate the observed problem on a laboratory scale, 142; 3) develop options for fixing (correcting) the observed problem and test these on a laboratory scale, 144; and 4) validate the options(s) chosen for correcting the observed problem prior to implementing the correction when reinitiating full-scale production, 146. These are outlined in FIG. 14.

The first step is to diagnose the root cause of the streaking problem, 140. It may be tempting to skip this step and proceed directly to trying possible solutions. In the long run, however, understanding the root cause of the defect will suggest possible remedies, streamline the correction process, and add to the knowledge base used to correct future problems. Further, understanding the root cause is crucial in order to successfully duplicate the discoloration in the lab at 142.

At 140, a number of flawed (bad lot 1402) production parts are analyzed in two ways. First, the on-and off-color regions are measured 1404 using spatially resolved spectrometer 1 to determine the magnitude of the discoloration. On-color refers to the desired color of the part. Off-color refers to a "wrong" or "off" color, which is often found on or near a streaked region. Next, the same regions are subjected to morphological characterization 1406 via techniques such as optical microscopy, and scanning electron and/or transmission electron microscopy, as appropriate. Morphological characterization looks at the underlying, microscopic resin structure, including component dispersion and component size, shape and orientation, etc. Different morphologies on- and off-streak suggest hypotheses 1408 regarding a root cause. Examples of root causes for appearance flaws include pigment agglomeration, variation or abnormality in dispersed phase size or orientation, resin degradation, voiding, crazing or cracking, flow instabilities, gels, un-melts, contamination, and surface attrition.

Then, at 1410, theoretical models implemented via a computerized device may be used to help a user of this method and apparatus test the hypothesis 1408 that the observed morphologies might typically lead to the observed appearance. Examples of theoretical models used to test hypothesis 1408 include Mie scattering, Kubelka Munk and radiative transfer theory. The process to use these models starts by transforming the output from the morphological characterization into theoretical model inputs. These inputs include the concentrations, real and imaginary refractive index, size, shape, and orientation of the matrix, dispersed phases, and all particles observed in the morphological characterization. These inputs are fed into a computer algorithm implemented by a computerized device which uses one of the theoretical models to produce theoretical model output which includes the amount of light and color that is reflected, transmitted and adsorbed by the material. Running the computer algorithm twice using the inputs found both on- and off-streak gives a color difference that can be compared to the color difference measured using spatially resolved spectrometer 1. The hypothesis can then be accepted or rejected depending upon the substantial agreement between the theoretical model and the results from spatially resolved spectrometer 1, within a given confidence limit. If the hypothesis is rejected 1411, it may be modified and re-tested as needed. It is to be noted that some of the specified functions may be performed by the operator. For example, the computer may not necessarily compare the output with the hypothesis; it may provide output for analysis by the operator.

Once the hypothesis has been accepted 1412, the next step is to duplicate the identified production problem on a small scale and on parts which are more easily manipulated for analysis and testing, 142. It is preferable to invest the time to duplicate the problem rather than to do all testing and analysis on flawed production parts for three reasons. First, production equipment is not tied up while the problem is addressed. Second, production parts often have textures and shapes that make it difficult to perform appearance analysis. Third, many more formulations and conditions can be tested at lower cost and with less waste using smaller scale parts.

It is not sufficient, however, to generate small scale parts that simply mimic the appearance of the flawed production parts; the underlying cause of the streaking must be identical for this approach to work. The same resin that created appearance problems (1402) in production is molded using molding tool 2 in the laboratory. Molding tool inserts 31, 32, 33, 34, 35, 36, etc., are chosen as described earlier to duplicate key topological features of the defective production parts, and laboratory-scale parts 11 are molded 1420. Importantly, processing conditions are chosen that are comparable on the small scale to the processing conditions used in production (mold dwell time, resin temperature, etc.).

Streaking on the laboratory sample plastic parts 11 is quantified 1422 using the spatially resolved spectrometer 1 and the tools and approaches earlier identified in connection with FIGS. 1 through 13. At 1424, the morphology of these small samples is checked to verify that the streaking has the same apparent cause in the laboratory and in production. Only after both the color difference and the morphology on the small-scale samples matches the production pieces (1426, 1428), is the user ready to proceed to identifying possible corrective actions. At various times through these first two steps the user may need to refine the hypothesis 1408 and/or vary the mold tool or mold conditions used to produce laboratory molds 1420, to accurately diagnose and replicate the discoloration problem.

Now, the third main step begins, wherein possible solutions for fixing (correcting) the observed problem are developed and tested on a laboratory scale 144. After a test plan is developed 1440, a design of experiments (DOE) is generated at 1442. DOE is a technique for multivariate analysis that eliminates both the practice of varying only one variable at a time and the need to test each possible combination. Instead multiple variables are changed simultaneously according to a predetermined test matrix. This is described, for example, in *Statistics for Experimenters* by George E. P. Box, William G. Hunter and J. Stuart Hunter, John Wiley and Sons, 1978, see particularly Part III: Measuring the Effects of Variables, pages 291–432. In addition, Chapter 15: Response Surface Methods, pages 510–535, is particularly useful.

DOE 1442 uses combinations of resin formulation and processing conditions as variables. Possible variables include, but are not limited to, pigment or component type, choice, manufacturer, quantity, and molecular weight, mixing conditions, and extruder conditions such as temperature or flow. Molding tool 2 is used to generate multiple plaques (sample molded plastic parts 11) for each DOE point, and the degree of streaking (or discoloration) on these samples is quantified 1444 to generate a response surface 1446 that relates the degree of streaking (or appearance) to resin formulation and processing conditions, using spectrometer 1 and the techniques and tools of FIGS. 1 through 13 as earlier described. Various areas of the response surface may then be examined in greater detail or new areas explored at 1448, based on the initial analysis, in an iterative process. The outcome of this analysis is (a set of) improved formulations that show better performance in a wider range of processing conditions. Note that the resin that is deemed "best" might have slightly lesser, optimum streaking performance, but might be more stable in general; experiments and analysis should be carefully designed to fully understand resin performance under a range of conditions.

Once "good" formulation candidates have been identified, the final main step begins, wherein the options(s) chosen for correcting the observed problem are validated prior to reinitiating full-scale production, 146. Unstreaked samples are morphologically analyzed at 1460 to verify that the underlying streaking problem has been solved. This is important for two reasons: 1) to "close the loop" and verify the initial hypothesis as to the root cause of the streaking, 1462, thus allowing more rapid resolution of similar problems on different products or platforms in the future; and 2) to verify that the problem has been solved rather than simply masked by additional pigment or some other temporary "fix." The danger in skipping this step is that the problem may recur if conditions change even slightly. A robust solution is tolerant of a wide range of processing conditions and does not display "pathological" morphology.

At 1464, the chosen solution is tested at full-scale using production equipment including a production mold. The new resin is run to create production parts under normal (and possibly near-normal) conditions to verify that scale-up will be successful. If desired, several candidates may be tested at full-scale to determine if there are any significant differences between them. Recall that earlier, it was necessary to choose "comparable" processing conditions for small-scale duplication of the problem. Through the entire correction procedure, attention must be paid to processing conditions for this step to be successful. These parts are then tested at 1466 to determine if the chosen solution will work properly in full-scale production. If this fails, the original hypothesis 1408 may need to be refined 1468 and a new DOE conducted at 1442 and 144 generally.

Finally, at 1470, once the chosen solution has been validated, full scale production is resumed.

In the above, it is to be observed that sample plastic parts 11 are produced at the second, third, and possibly fourth of the aforementioned mains steps. At 1420, one or more sample plastic parts 11 are produced to reproduce defects in bad lot 1402, which will be referred to as "defect-reproducing" sample plastic parts 11. In 144 generally, "option-testing" sample plastic parts 11 are produced to test options for correcting the production defects. And in 146 generally, "corrective-testing" sample plastic parts 11 are produced which implement the chosen correction, as a basis for validating that chosen solution. The corrective-testing sample parts may, however, in some instances, simply comprise one or more of the option-testing samples produced in 144 which are determined to be good options for production-scale implementation. Finally, also in 146, "scaled up" sample plastic parts 11 are produced which are used to validate the chosen solution prior to full-scale resumption of production.

While only certain preferred features of the invention have been illustrated and described, many modifications, changes and substitutions will occur to those skilled in the art. It is, therefore, to be understood that the appended claims are intended to cover all such modifications and changes as fall within the true spirit of the invention.

What is claimed is:

1. A system to improve streaking performance in molded plastic parts (11), comprising:

a molding tool (2) for producing sample plastic parts (11);

a spatially-resolved spectrometer (1) obtaining a plurality of raw data (50) readings of reflected light (14) from sample points (17) of plastic parts (11);

a computerized device (101) for post-processing said raw data (50) readings by analyzing and quantifying said readings (50);

morphological characterization means (1406, 1424, 1460, 1466) to determine and characterize morphology of plastic parts (11); and morphology comparison means for obtaining comparison (1428) between morphologies of a plurality of plastic parts (11); wherein:

a streaking problem from a defective production lot (1402) is diagnosed (140) and at least one hypothesis (1408) is formed and validated (1412) regarding a root cause of said streaking problem;

once said at least one hypothesis (1408) has been validated (1412), said streaking problem is replicated on a laboratory scale (142) until a substantial color match (1426) and a substantial morphological match (1428) are obtained between said streaking problem in said defective production lot (1402) and streaking in at least one defect reproducing sample plastic part (11) designed to replicate said streaking problem (1420);

once said substantial color and morphological matches (1426, 1428) are obtained, possible solutions for correcting said streaking problem are developed and tested on a laboratory scale (144), and at least one optimal solution is identified for correction of said streaking problem (1448); and once said at least one optimal solution is identified (1448), said optimal solution is validated and then implemented (146) in full-scale production (1470).

2. The system of claim 1, wherein to diagnose (140) said streaking problem and form and validate (1412) said at least one hypothesis (1408) regarding a root cause of said streaking problem:

said spatially resolved spectrometer (1) is used to measure a magnitude of discoloration (1404) of at least one region of defective plastic parts (11) of said defective production lot (1402);

said morphological characterization means (1406, 1424, 1460, 1466) is used to subject the same at least one region of said defective plastic parts (11) to morphological characterization (1406); and a second computerized device uses at least one theoretical model of relationships between observed morphologies and observed appearances (1410, 1412) to assist a user of said system to test and validate said at least one hypothesis (1408) regarding a root cause of said streaking problem.

3. The system of claim 2, wherein said second computerized device further comprises means to:

transform output from said morphological characterization means (1406, 1424, 1460, 1466) into theoretical model input;

use said theoretical model input to deduce amounts of light and color that should be reflected, transmitted and adsorbed by said defective plastic parts (11), for each of on-streak and off-streak regions of said defective plastic parts (11), resulting in a theoretical model output;

compare said theoretical model output with said measurement of said magnitude of discoloration (1404) of said defective plastic parts (11); and validate said at least one hypothesis (1408) if said theoretical model output is in substantial agreement with said measurement of said magnitude of discoloration (1404) of said defective plastic parts (11).

4. The system of claim 1, wherein to replicate said streaking problem on a laboratory scale (142):

said molding tool (2) is used to produce said at least one defect reproducing sample plastic part (11);

said spatially resolved spectrometer (1) is used to measure a magnitude of discoloration (1422) of at least one region of said at least one defect reproducing sample plastic part (11);

said morphological characterization means (1406, 1424, 1460, 1466) is used to subject the same at least one region of said at least one defect reproducing sample plastic part (11) to morphological characterization (1424);

said magnitude of discoloration (1404) of said defective production lot (1402) is compared to said magnitude of discoloration (1422) of said defect reproducing sample plastic part (11) until said substantial color match is obtained (1426), using said morphology comparison means; and said morphological characterization (1406) of said defective production lot (1402) is compared to said morphological characterization (1424) of said defect reproducing sample plastic part (11) until, said substantial morphological match is obtained (1428), using said morphology comparison means.

5. The system of claim 1, wherein to develop and test said possible solutions for correcting said streaking problem on a laboratory scale (144), and to identify said at least one optimal solution is for correction of said streaking problem (1448):

a design of experiments (1442) is conducted to generate options for correcting said streaking problem;

said molding tool (2) is used to produce at least one option testing sample plastic part (11);

said spatially resolved spectrometer (1) is used to measure a magnitude of discoloration (1444) of at least one region of said option testing sample plastic parts (11);

a response surface (1446) is generated therefrom that relates plastic parts (11) appearance to resin formulations and processing conditions used to produce plastic parts (11); and said at least one optimal solution for correction of said streaking problem (1448) is identified.

6. The system of claim 1, wherein to validate and implement (146) said optimal solution:

said morphological characterization means (1406, 1424, 1460, 1466) are used to subject at least one region of at least one corrective testing sample plastic part (11) to morphological characterization (1460) until it is determined that said optimal solution does in fact correct said root cause of said streaking problem (1462);

once it is determined that said optimal solution does in fact correct said root cause of said streaking problem (1462):

a production mold is used to produce at least one scaled up sample plastic part, based on said optimal solution (1464);

said spatially resolved spectrometer (1) is used to measure a magnitude of discoloration (1466) of at least one region of said scaled up sample plastic part (11); and said morphological characterization means (1406, 1424, 1460, 1466) is used to subject the same at least one region of said scaled up sample plastic part (11) to morphological characterization (1466);

until it is determined that said optimal solution also works properly when scaled up (1468); and once it is determined that said optimal solution also works properly when scaled up (1468):

said full-scale production is resumed (1470):.

7. The system of claim 1, wherein said morphological characterization means (1406, 1424, 1460, 1466) is selected from a morphological characterization means group consisting of at least one of:

at least one optical microscope;

at least one scanning electron microscope; and at least one transmission electron microscope.

8. The system of claim 1, wherein said molding tool (2) further comprises:

a cavity (21, 22) comprising at least one gate (37), wherein molten plastic is extruded through said at least one gate (37) into said cavity (21, 22) to so-produce said sample plastic parts (11) with any appearance defects resulting from said extrusion through said at least one gate (37).

9. The system of claim 1, wherein said molding tool (2) further comprises:

a cavity (21, 22) comprising at least one gate (37) and at least one insert location (26); and at least one molding tool insert (3) with at least one negative topological feature thereof, inserted into said at least one insert location (26); wherein molten plastic is extruded through said gate (37) into said cavity (21, 22) to so-produce said sample plastic parts (11) with positive topological surface features corresponding to said negative topological features of said at least one molding tool insert (3), and with any appearance defects resulting from said positive topological surface features.

10. The system of claim 9, wherein said negative and corresponding positive topological features are selected from a topological feature group consisting of:

a flat, null surface;

a hole (31);

a boss (32);

a rib at an angle between zero and 45 degrees (33) relative to said extrusion of said molten plastic through said gate (37);

a rib at an angle between 45 and 90 degrees (34) relative to said extrusion of said molten plastic through said gate (37);

a grill at an angle between zero and 45 degrees (35) relative to said extrusion of said molten plastic through said gate (37); and a grill at an angle between 45 and 90 degrees (36) relative to said extrusion of said molten plastic through said gate (37).

11. The system of claim 1, wherein said computerized device (101) further comprises:

computerized data compression means (511) for calculating compressed data by filtering out local noise below a predetermined threshold, from said raw data (50);

computerized first iteration filtering means (512) for calculating first iteration filtered data by identifying local extreme points comprising maximum and minimum points in said compressed data;

computerized second iteration filtering means (513) for calculating second iteration filtered data by removing from said first iteration filtered data, any of said local extreme points that vary with respect to an adjacent local extreme point by a magnitude below a predetermined limiting value; and computerized third iteration filtering means (513) for calculating a final iteration filtered data graph by returning to said second iteration filtered data, any minimum point that has an adjacent high maximum point on one side thereof and an adjacent low maximum point on an other side thereof.

12. The system of claim 11, wherein said computerized device (101) further comprises:

computerized quality calculation means for calculating (514) and linearizing (515) from said final iteration filtered data graph, a quality number Q given by:

$$Q = ln(M * \Sigma dL/dx),$$

where $\Sigma dL/dx$ represents a sum of slopes of said final iteration filtered data and M is a linearization multiplier.

13. The system of claim 11, wherein said computerized device (101) further comprises:

computerized shape calculation means for deriving (522) from said final iteration filtered data graph, at least one data shape descriptor selected from a data shape descriptor group consisting of:

a height of at least one of said maximum points with respect to at least one minimum point adjacent thereto;

a slope of said filtered data graph between at least one of said maximum points and at least one minimum point adjacent thereto;

a width of said filtered data graph between at least one pair of selected local extreme points; and a curve shape of at least one region of said filtered data graph.

14. The system of claim 1, wherein said computerized device (101) further comprises:

computerized data compression means (531) for calculating compressed data by filtering out local noise below a predetermined noise threshold, from said raw data (50), and by identifying (532) local extreme points comprising maximum and minimum points in said raw data (50); and computerized shift calculation means for calculating (533) an average peak height of said local extreme points of said compressed data, wherein the average shift S in said peak heights is calculated as:

$$S=T/N,$$

where T represents a total sum of peak heights above a predetermined height threshold, and N represents a number of said peak heights above said predetermined height threshold.

15. A method for improving streaking performance in molded plastic parts (11), comprising the steps of:

diagnosing (140) a streaking problem from a defective production lot (1402) and forming and validating (1412) at least one hypothesis (1408) regarding a root cause of said streaking problem;

once said at least one hypothesis (1408) has been validated (1412), replicating said streaking problem on a laboratory scale (142) until a substantial color match (1426) and a substantial morphological match (1428) are obtained between said streaking problem in said defective production lot (1402) and streaking in at least one defect reproducing sample plastic part (11) designed to replicate said streaking problem (1420);

once said substantial color and morphological matches (1426, 1428) are obtained, developing and testing possible solutions for correcting said streaking problem on a laboratory scale (144), and identifying at least one optimal solution for correction of said streaking problem (1448); and once said at least one optimal solution is identified (1448), validating and then implementing (146) said optimal solution in full-scale production (1470), wherein said method utilizes:

a molding tool (2) for producing sample plastic parts (11);

a spatially-resolved spectrometer (1) obtaining a plurality of raw data (50) readings of reflected light (14) from sample points (17) of plastic parts 22 (11);

a computerized device (101) for post-processing said raw data (50) readings by analyzing and quantifying said readings (50);

morphological characterization means (1406, 1424, 1460, 1466) to determine and characterize morphology of plastic parts (11:); and morphology comparison means for obtaining comparison (1428) between morphologies of a plurality of plastic parts (11).

16. The method of claim 15, wherein the step of diagnosing (140) said streaking problem and forming and validating (1412) said at least one hypothesis (1408) regarding a root cause of said streaking problem, comprises the further steps of:

measuring a magnitude of discoloration (1404) of at least one region of defective plastic parts (11) of said defective production lot (1402), using said spatially resolved spectrometer (1) and said computerized device (101);

subjecting the same at least one region of said defective plastic parts (11) to morphological characterization (1406), using said morphological characterization means (1406, 1424, 1460, 1466); and assisting a user of said method in testing and validating said at least one hypothesis (1408) regarding a root cause of said streaking problem using at least one theoretical model of relationships between observed morphologies and observed appearances (1410, 1412), via a second computerized device.

17. The method of claim 16, wherein the step of assisting a user of said method in testing and validating said at least one hypothesis (1408) regarding a root cause of said streaking problem using at least one theoretical model of relationships between observed morphologies and observed appearances (1410, 1412), via said second computerized device, comprises the further steps of:

transforming output from said morphological characterization means (1406, 1424, 1460, 1466) into theoretical model input;

using said theoretical model input to deduce amounts of light and color that should be reflected, transmitted and adsorbed by said defective plastic parts (11), for each of on-streak and off-streak regions of said defective plastic parts (11), resulting in a theoretical model output;

comparing said theoretical model output with said measurement of said magnitude of discoloration (1404) of said defective: plastic parts (11); and validating said at least one hypothesis (1408) if said theoretical model output is in substantial agreement with said measurement of said magnitude of discoloration (1404) of said defective plastic parts (11).

18. The method of claim 15, wherein the step of replicating said streaking problem on a laboratory scale (142), comprises the further steps of:

using said molding tool (2) to produce said at least one defect reproducing sample plastic part (11);

measuring a magnitude of discoloration (1422) of at least one region of said at least one defect reproducing sample plastic part (11), using said spatially resolved spectrometer (1) and said computerized device (101);

subjecting the same at least one region of said at least one defect reproducing sample plastic part (11) to morphological characterization (1424), using said morphological characterization means (1406, 1424, 1460, 1466);

comparing said magnitude of discoloration (1404) of said defective production lot (1402) to said magnitude of discoloration (1422) of said defect reproducing sample plastic part (11) until said substantial color match is obtained (1426), using said morphology comparison means; and comparing said morphological characterization (1406) of said defective production lot (1402) to said morphological characterization (1424) of said defect reproducing sample plastic part (11) until said substantial morphological match is obtained (1428), using said morphology comparison means.

19. The method of claim 15, wherein the step of developing and testing said possible solutions for correcting said streaking problem on a laboratory scale (144), and of identifying said at least one optimal solution for correction of said streaking problem (1448), comprises the further steps of:
   conducting a design of experiments (1442) to generate options for correcting said streaking problem;
   producing at least one option testing sample plastic part (11) using said molding tool (2);
   measuring a magnitude of discoloration (1444) of at least one region of said option testing sample plastic parts (11), using said spatially resolved spectrometer (1) and said computerized device (101);
   generating therefrom a response surface (1446) that relates plastic parts (11) appearance to resin formulations and processing conditions used to produce plastic parts (11); and
   identifying said at least one optimal solution for correction of said streaking problem (1448).

20. The method of claim 15, wherein the step of validating and then implementing (146) said optimal solution, comprises the further steps of:
   subjecting at least one region of at least one corrective testing sample plastic part (11) to morphological characterization (1460), using said morphological characterization means (1406, 1424, 1460, 1466), until it is determined that said optimal solution does in fact correct said root cause of said streaking problem (1462);
   once it is determined that said optimal solution does in fact correct said root cause of said streaking problem (1462):
      producing at least one scaled up sample plastic part (1464), using a production mold, based on said optimal solution;
      measuring a magnitude of discoloration (1466) of at least one region of said scaled up sample plastic part (11), using said spatially resolved spectrometer and said computerized device (101); and
      subjecting the same at least one region of said scaled up sample plastic part (11) to morphological characterization (1466) using said morphological characterization means (1406, 1424, 1460, 1466);
      until it is determined that said optimal solution also works properly when scaled up (1468); and
   once it is determined that said optimal solution also works properly when scaled up (1468):
      resuming said full-scale production (1470).

21. The method of claim 15, comprising the further step of selecting said morphological characterization means (1406, 1424, 1460, 1466) from a morphological characterization means group consisting of at least one of:
   at least one optical microscope;
   at least one scanning electron microscope; and
   at least one transmission electron microscope.

22. The method of claim 15, said step of producing said sample plastic parts (11) using said molding tool (2) further comprising the step of:
   extruding molten plastic through at least one gate (37) into a cavity (21, 22) thereby so-producing said sample plastic parts (11) with any appearance defects resulting from said extrusion through said at least one gate (37).

23. The method of claim 15, said step of producing said sample plastic parts (11) using said molding tool (2) further comprising the steps of:
   inserting at least one molding tool insert (3) with at least one negative topological feature thereof, into at least one insert location (26) of a cavity (21, 22);
   extruding molten plastic through at least one gate (37) into said cavity (21, 22) thereby so-producing said sample plastic parts (11) with positive topological surface features corresponding to said negative topological features of said at least one molding tool insert (3), and with any appearance defects resulting from said positive topological surface features.

24. The method of claim 23, comprising the further step of selecting said negative and corresponding positive topological features from a topological feature group consisting of:
   a flat, null surface;
   a hole (31);
   a boss (32);
   a rib at an angle between zero and 45 degrees (33) relative to said extrusion of said molten plastic through said gate (37);
   a rib at an angle between 45 and 90 degrees (34) relative to said extrusion of said molten plastic through said gate (37);
   a grill at an angle between zero and 45 degrees (35) relative to said extrusion of said molten plastic through said gate (37); and
   a grill at an angle between 45 and 90 degrees (36) relative to said extrusion of said molten plastic through said gate (37).

25. The method of claim 15, said step of analyzing and quantifying said readings (50) by post-processing said raw data (50) readings using said computerized device (101) comprising the further steps of:
   calculating compressed data (511) from said raw data (50) by filtering out local noise below a predetermined threshold;
   calculating first iteration filtered data (512) by identifying local extreme points comprising maximum and minimum points in said compressed data;
   calculating second iteration filtered data (513) by removing from said first iteration filtered data, any of said local extreme points that vary with respect to an adjacent local extreme point by a magnitude below a predetermined limiting value; and
   calculating a final iteration filtered data graph (513) by returning to said second iteration filtered data, any minimum point that has an adjacent high maximum point on one side thereof and an adjacent low maximum point on an other side thereof.

26. The method of claim 25, comprising the further step of:
   calculating (514) and linearizing (515) from said final iteration filtered data graph, a quality number Q given by:

$$Q = ln(M * \Sigma dL/dx),$$

where $\Sigma dL/dx$ represents a sum of slopes of said final iteration filtered data and M is a linearization multiplier.

27. The method of claim 25, comprising the further steps of:

deriving (522) from said final iteration filtered data graph, at least one data shape descriptor selected from a data shape descriptor group consisting of:

a height of at least one of said maximum points with respect to at least one minimum point adjacent thereto;

a slope of said filtered data graph between at least one of said maximum points and at least one minimum point adjacent thereto;

a width of said filtered data graph between at least one pair of selected local extreme points; and a curve shape of at least one region of said filtered data graph.

28. The method of claim 15, said step of analyzing and quantifying said readings (50) by post-processing said raw data (50) readings using said computerized device (101) comprising the further steps of:

calculating compressed data (531) by filtering out local noise below a predetermined noise threshold, from said raw data (50), and by identifying (532) local extreme points comprising maximum and minimum points in said raw data (50); and calculating (533) an average peak height of said local extreme points of said compressed data, wherein the average shift S in said peak heights is calculated as:

$$S=T/N,$$

where T represents a total sum of peak heights above a predetermined height threshold, and N represents a number of said peak heights above said predetermined height threshold.

* * * * *